(12) United States Patent
Yamashiro (10) Patent No.: US 10,610,685 B2
(45) Date of Patent: Apr. 7, 2020

(54) SMOOTH MUSCLE ELECTRICAL STIMULATION BASED ON ENTRAINMENT OF INTRACELLULAR CALCIUM ION OSCILLATIONS

(71) Applicant: University of Southern California, Los Angeles, CA (US)

(72) Inventor: Stan Yamashiro, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 190 days.

(21) Appl. No.: 15/849,506

(22) Filed: Dec. 20, 2017

(65) Prior Publication Data

US 2018/0169409 A1  Jun. 21, 2018

Related U.S. Application Data

(60) Provisional application No. 62/437,577, filed on Dec. 21, 2016.

(51) Int. Cl.
*A61N 1/36* (2006.01)
*A61N 1/04* (2006.01)
*A61N 1/372* (2006.01)
*A61N 1/05* (2006.01)

(52) U.S. Cl.
CPC ....... *A61N 1/36007* (2013.01); *A61N 1/0452* (2013.01); *A61N 1/0456* (2013.01); *A61N 1/0509* (2013.01); *A61N 1/0512* (2013.01); *A61N 1/3606* (2013.01); *A61N 1/36034* (2017.08); *A61N 1/36178* (2013.01); *A61N 1/37211* (2013.01)

(58) Field of Classification Search
CPC .................. A61N 1/36007; A61N 1/0452
USPC .......................................... 607/40
See application file for complete search history.

(56) References Cited

U.S. PATENT DOCUMENTS 3,870,051 A * 3/1975 Brindley ............ A61N 1/36007
607/40

OTHER PUBLICATIONS

J. Huizinga et al.; *"Pacemaker Activity in the Proximal Lower Oesophageal Sphincter of the Dog"*; Journal of Physiology, 1989, 408, pp. 19-30 (12 pages).
S. Sims et al.; *"Calcium Sensitization in Human Esophageal Muscle: Role for RhoA Kinase in Maintenance of Lower Esophageal Sphincter Tone"*; Journal of Pharmacology and Experimental Therapeutics, vol. 327, No. 1, 2008 (9 pages).

(Continued)

*Primary Examiner* — Nadia A Mahmood
(74) *Attorney, Agent, or Firm* — Snell & Wilmer LLP (57) ABSTRACT

Methods, systems, and apparatus for electrically stimulating a smooth muscle. The method includes generating a continuous pulse train signal having pulses and pulse intervals between the pulses, the pulses and the pulse intervals being generated at a pulse frequency. The method also includes modulating the continuous pulse train signal at a modulation frequency to match dynamics of intracellular calcium ion oscillations in the smooth muscle. The method also includes entraining a group of cells of the smooth muscle by applying the modulated continuous pulse train signal to the group of cells of the smooth muscle to increase an oscillation frequency of the calcium ion oscillations.

19 Claims, 7 Drawing Sheets

(56) References Cited

OTHER PUBLICATIONS

Hikaru Hashitani; "*Interaction Between Interstitial Cells and Smooth Muscles in the Lower Urinary Tract and Penis*"; Journal the Physiological Society, 576.3, 2006, pp. 707-714 (8 pages).

L. Bursztyn et al.; "*Mathematical Model of Excitation-Contraction in a Uterine Smooth Muscle Cell*"; American Journal Physiology Cell Physiology, 292, 2007, pp. C1816-C1829 (14 pages).

A. Corrias et al.; "*A Quantitative Model of Gastric Smooth Muscle Cellular Activation*"; Annals of Biomedical Engineering, vol. 35, No. 9, Sep. 2007, pp. 1595-1607 (13 pages).

C. Hai et al.; "*Cross-Bridge Phosphorylation and Regulation of Latch State in Smooth Muscle*"; American Physiological Society; 1988 (8 pages).

P. Du et al.; "*Effects of Electrical Stimulation on Isolated Rodent Gastric Smooth Muscle Cells Evaluated Via a Joint Computational Simulation and Experimental Approach*"; Americal Journal Physiology Gastrointest Liver Physiology, 297, 2009, pp. G672-G680 (9 pages).

\* cited by examiner

SMOOTH MUSCLE ELECTRICAL STIMULATION BASED ON ENTRAINMENT OF INTRACELLULAR CALCIUM ION OSCILLATIONS

CROSS REFERENCE TO RELATED APPLICATIONS

This application claims the benefit and priority of U.S. Provisional Application Ser. No. 62/437,577, filed on Dec. 21, 2016, entitled "Smooth Muscle Electrical Stimulation Based on Entrainment of Intracellular Calcium Ion Oscillations," the contents of which are herein incorporated by reference in its entirety.

BACKGROUND

1. Field

This specification relates to a system and a method for electrically stimulating smooth muscles.

2. Description of the Related Art

Conventional systems and methods for inducing contraction of sphincters focus on applying a continuous electrical stimulation to the sphincter. However, continuous electrical stimulation directly to the sphincter is not effective for sustained contraction of the sphincter. Accordingly, there is a need for an improved system and method for inducing contraction of sphincters.

SUMMARY

What is described is a method for electrically stimulating a smooth muscle. The method includes generating a continuous pulse train signal having pulses and pulse intervals between the pulses, the pulses and the pulse intervals being generated at a pulse frequency. The method also includes modulating the continuous pulse train signal at a modulation frequency to match dynamics of intracellular calcium ion oscillations in the smooth muscle. The method also includes entraining a group of cells of the smooth muscle by applying the modulated continuous pulse train signal to the group of cells of the smooth muscle to increase an oscillation frequency of the calcium ion oscillations.

Also described is a system for electrically stimulating a sphincter. The system includes a stimulator having a housing designed to be implanted in or worn on a mammal and having a power transmitter designed to output a continuous pulse train signal having pulses and pulse intervals between the pulses. The system also includes at least one electrode electrically coupled to the power transmitter and designed to be coupled to a location near the sphincter and to transmit the continuous pulse train signal to the location near the sphincter to enhance closure of the sphincter.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale, and may be exaggerated to better illustrate the important features of the present invention.

DETAILED DESCRIPTION

Disclosed herein are systems and methods for electrically stimulating smooth muscles.

Prior use of electrical stimulation for medical therapy has largely followed the approach of the cardiac pacemaker. Pulses of voltage or current of different durations and repetition frequencies have been used for the purpose of depolarizing nerves, muscle, or smooth muscle to achieve a therapeutic goal. Nerve and muscle respond to such depolarizations when threshold levels are reached with an all-or-none action potential response. A strength-duration curve is typically sufficient to predict responses to a single stimulating pulse. However, certain excitable tissues, such as smooth muscle, do not respond in an all-or-none fashion but respond in a graded way where intracellular calcium ion concentrations oscillate at a spontaneous frequency which can vary in proportion to the level of stimulation. Intracellular calcium concentration is known to be responsible for smooth muscle contraction.

A burst or intermittent pulse train has been previously used primarily as a way to lower power consumption, but not as a way to enhance contraction. The electrical stimulation proposed herein entrains or synchronizes calcium intracellular oscillations to enhance the desired output of stimulation.

Some smooth muscles naturally act as sphincters which contract continuously for extended periods without requiring continuous neural input. Sphincters may receive input from Interstitial Cells of Cajal, a type of interstitial cell found in the gastrointestinal (GI) tract, which then locally promote the calcium oscillations. As used herein, the target of stimulation is not conventional depolarization, but rather enhanced output achieved by entrainment of local oscillators followed by gradual increase in the frequency of oscillation of the entire smooth muscle sphincter complex.

Conventional electrical stimulation may involve stimulation of a single excitable cell. In contrast, the systems and methods described herein target an entire group of cells. Individual smooth cells are known to be capable of independent oscillatory behavior, but what is disclosed herein is how to synchronize or entrain these oscillations in order to enhance their collective output. Unlike conventional approaches, in the systems and methods described herein, no phase response mapping is used and the systems and methods are intended to synchronize and enhance the frequency of oscillation, not to eliminate oscillation. Experimental results show a 350% increase in smooth muscle closing pressure as compared with a 27% increase using conventional stimulation. Thus, a more than 10-fold enhancement is possible using the systems and methods described herein. This result is completely unexpected to those skilled in the art and thus not obvious.

Figure 7:
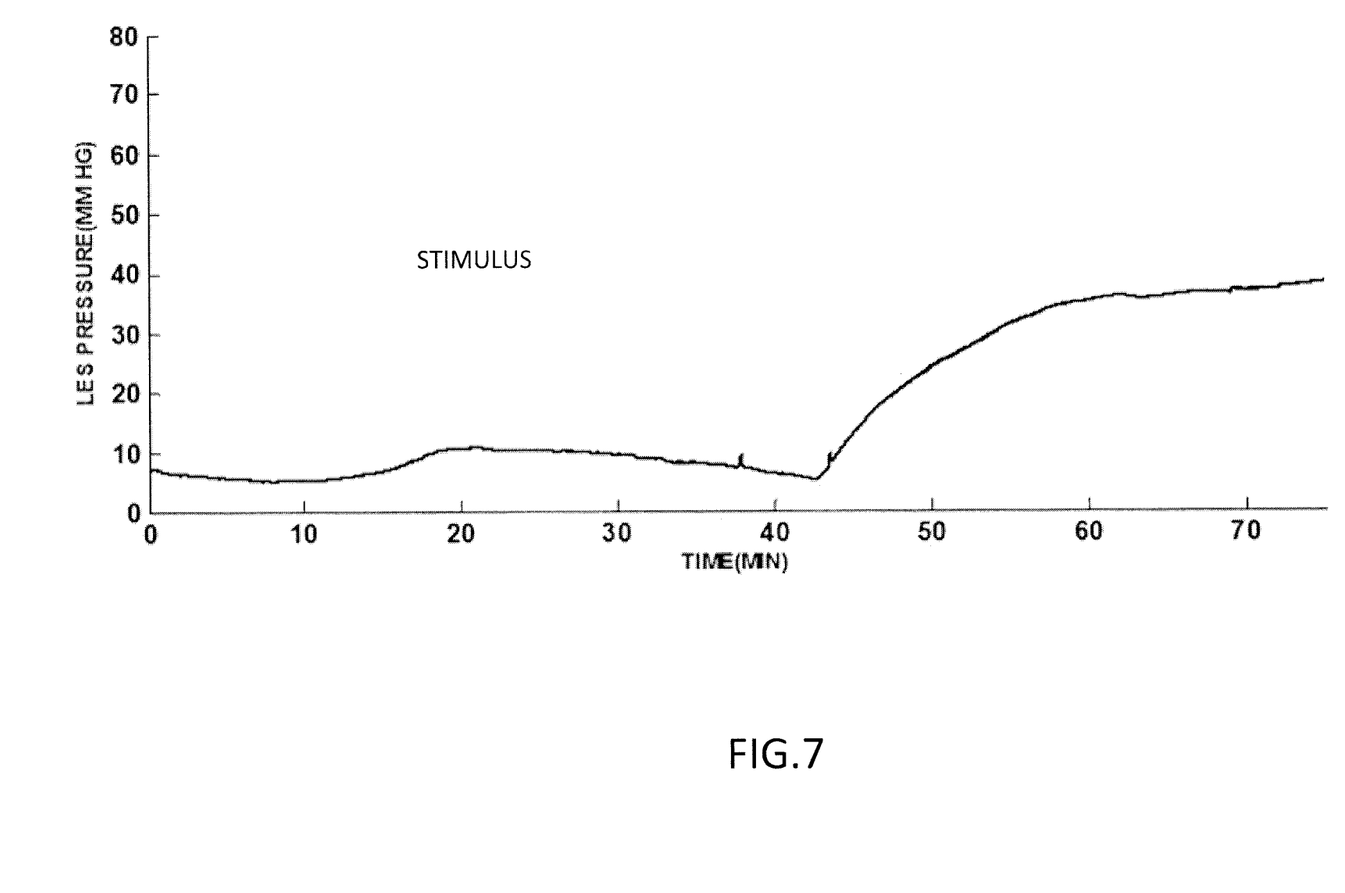
FIG. 7 illustrates measured response of closing pressure in the esophagus in response to a second set of stimulation parameters, according to various embodiments of the invention.

The present invention is a system and a method for stimulating the pacemaker region also called the Interstitial Cells of Cajal, which is anatomically distinct from the lower esophageal sphincter. The subject inventive device functionally affects the lower esophageal sphincter, but not by direct electrical stimulation. In fact, in the experimental results, using 5 mA of stimulation led to inhibiting lower esophageal sphincter contraction during the period of stimulation, but led to increased esophageal sphincter contraction afterwards, as illustrated in FIG. 7. This demonstrates the difference between sites of stimulation. Only the pacemaker region is electrically stimulated in the systems and methods described herein.

There are many medical applications whereby inadequate contraction of smooth muscle can be treated by the systems and methods described herein. GERD (gastroesophageal reflux disease) is due to inadequate closure of the lower esophageal sphincter (LES). While previous approaches target the LES alone, the systems and methods described herein instead target the pacemaker or oscillatory region (Interstial Cells of Cajal) which is known by those skilled in the art to be located proximal to the LES region.

The systems and methods described herein may be used to treat incontinence by targeting pacemaker regions corresponding to urethral sphincters. Electrical stimulation has previously been used to treat incontinence by directly targeting smooth muscle sphincters. For example, electrical nerve stimulation may be performed on sacral nerves for this purpose. Again, this is distinct from the systems and methods described herein because the target of stimulation of the systems and methods described herein is not nerves, but the pacemaker cells. Nerve stimulation is not needed for pacemaker cell activation, which can be independently stimulated. In fact, administration of Tetrodotoxin (a well-known drug that blocks all nerve conduction) may actually increase pacemaker cell activity. Interstitial Cells of Cajal are known to be present near these sphincters and may serve a similar pacemaker role as those associated with the lower esophageal sphincter described herein. Thus, treating incontinence is another useful application of the systems and methods described herein. Incontinence treatment by electrical stimulation by conventional systems suffers from unreliable sphincter contraction, as evidenced by current clinical trial "success" being defined as 50% control of incontinence. In other words, it fails half of the time. Entrainment of the pacemaker cells related to incontinence has never been previously targeted using electrical stimulation. Bursts of pulses or intermittent stimulation have been tried clinically to treat incontinence, but entrainment was not the goal and the stimulation parameters tried were incompatible with entrainment. Contraction responses equal to continuous stimulation have been reported.

Urinary incontinence is another possible application where the sacral nerve is electrically stimulated. In some situations, during the period of electrical stimulation, the LES is relaxed and not contracted. Contraction usually occurs after the electrical stimulation is removed. The pacemaker region and entrainment is what is more effective for net LES closure. Thus, the precise timing of on-and-off stimulation periods is far more effective than continuous stimulation. The urethral sphincter has similar pacemaker type characteristics as the LES. Therefore, the current inventive device could be used to enhance urethral sphincter closure by entrainment of the urethral pacemaker.

Electrical stimulation in general becomes more effective as the amplitude of stimulation is increased. However, this strategy is ineffective because of stimulation of pain sensors which have similar threshold levels. This limitation usually significantly decreases stimulation effectiveness. For the specific application of GERD treatment, this has led to the marginally effective 27 percent increase in LES closing pressure mentioned herein. Using the same power level of stimulation, the new method of pacemaker entrainment led to a 350 percent improvement.

Figure 1:
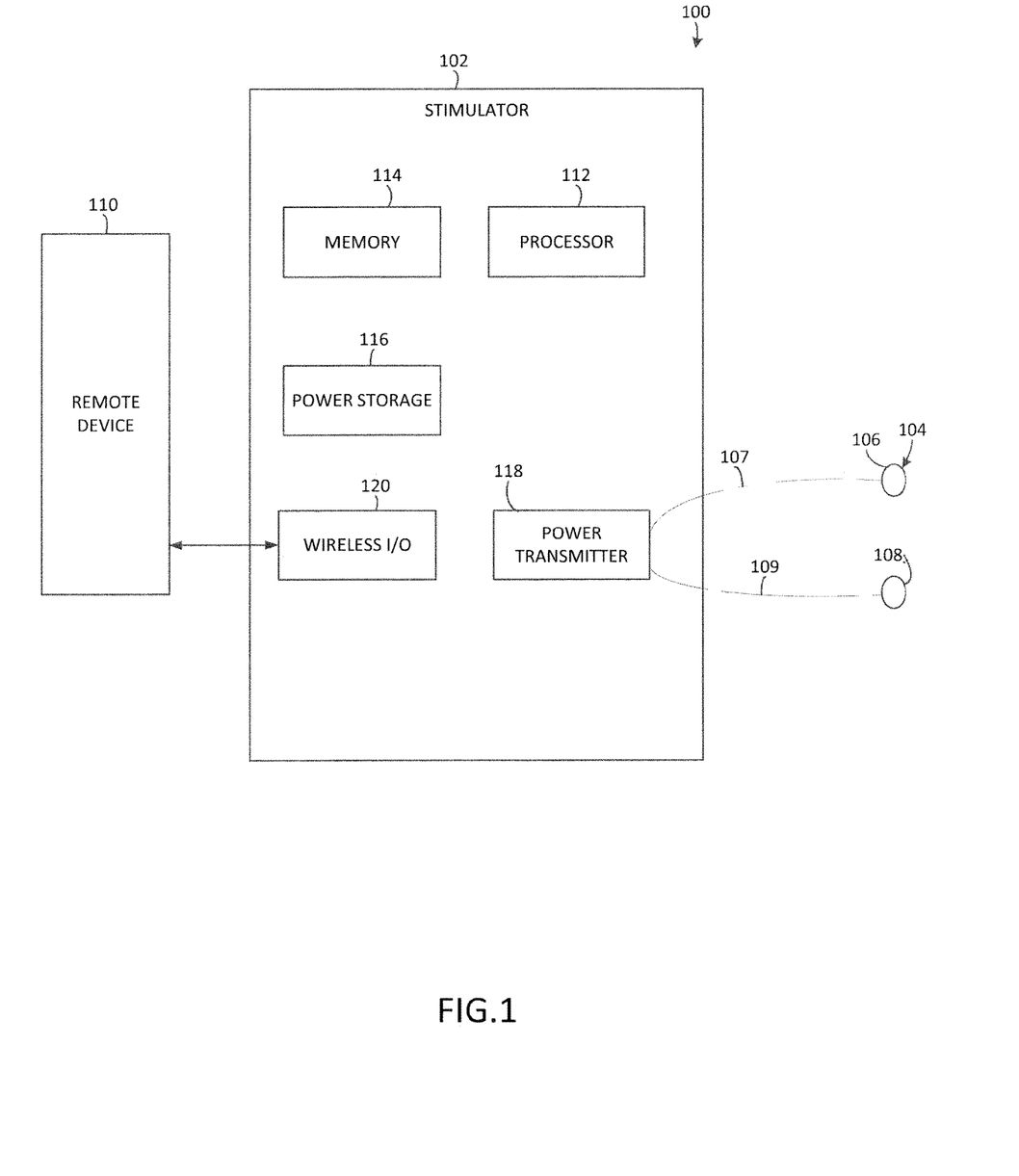
FIG. 1 illustrates a system for enhancing sphincter closure via entrainment, according to various embodiments of the invention.

Referring to FIG. 1, a system 100 for enhancing sphincter closure via entrainment is shown. The system 100 may be used to increase pressure applied by a sphincter within a gastrointestinal (GI) tract of the mammal. For example, the system 100 may be used to increase pressure applied by a sphincter located between and esophagus and a stomach to reduce acid reflux experienced when stomach acid extends through the sphincter entity esophagus. As other examples, the system 100 may be used to increase pressure applied by a sphincter located between an anal canal and an anus or between bladder and urine output in order to reduce incontinence.

The system 100 may include a stimulator 102 and one or more electrode 104. For example, the electrodes 104 may include a 1st electrode 106 and a 2nd electrode 108 coupled to the stimulator 102 via a 1st lead 107 and a 2nd lead 109, respectively.

In some embodiments, the system 100 may include a remote device 110 capable of providing updates or otherwise controlling the stimulator 102. For example, the remote device 110 may include any remote device, such as a handheld computer, a tablet, a laptop, or the like, capable of communicating with the stimulator 102 via a wireless protocol.

The stimulator 102 may include a housing 101, a processor 112, a memory 114, a power storage 116, a power transmitter 118, and a wireless input-output port 120.

The housing 101 may be designed to be implanted in a human body. In that regard, the material of the housing 101 may include any material capable of being stored or located within a mammal body without causing prolonged harm or discomfort to the mammal or significant harm to the material. For example, the material may include a metal, a plastic, or the like. In some embodiments, the housing 101 may be worn outside of the body with the leads 107, 109 located partially inside the body and the electrodes 104 located fully inside the body.

The processor 112 may include any processor, controller, or other logic device capable of performing logic. The memory 114 may include any non-transitory memory storage device capable of storing data. In that regard, the data stored in the memory 114 may be utilized by the processor 112. For example, the memory 114 may store instructions usable by the processor 112 to perform functions, such as one or more functions described below with reference to FIG. 4.

The power storage 116 may include any power storage device such as a battery, a super capacitor, or the like. The power storage 116 may be capable of storing electrical energy usable to power components of the stimulator 102. For example, the power storage 116 may be capable of outputting analog current (AC) electrical power or direct current (DC) electrical power.

The power transmitter 118 may include any device capable of transmitting electrical power to the electrodes 104 via the leads 107, 109. In some embodiments, the power transmitter 118 may include a switch (such as a transistor or other switch), a conductor (such as a wire or cable), or the like.

The processor 112 may be designed to generate or identify a continuous pulse train signal having pulses and pulse intervals. For example, a pattern of the signal may be stored in the memory 114. The processor 112 may control at least one of the power storage device 116 or the power transmitter 118 to output the continuous pulse train signal to the electrodes 104 via the leads 107, 109.

Figure 2:
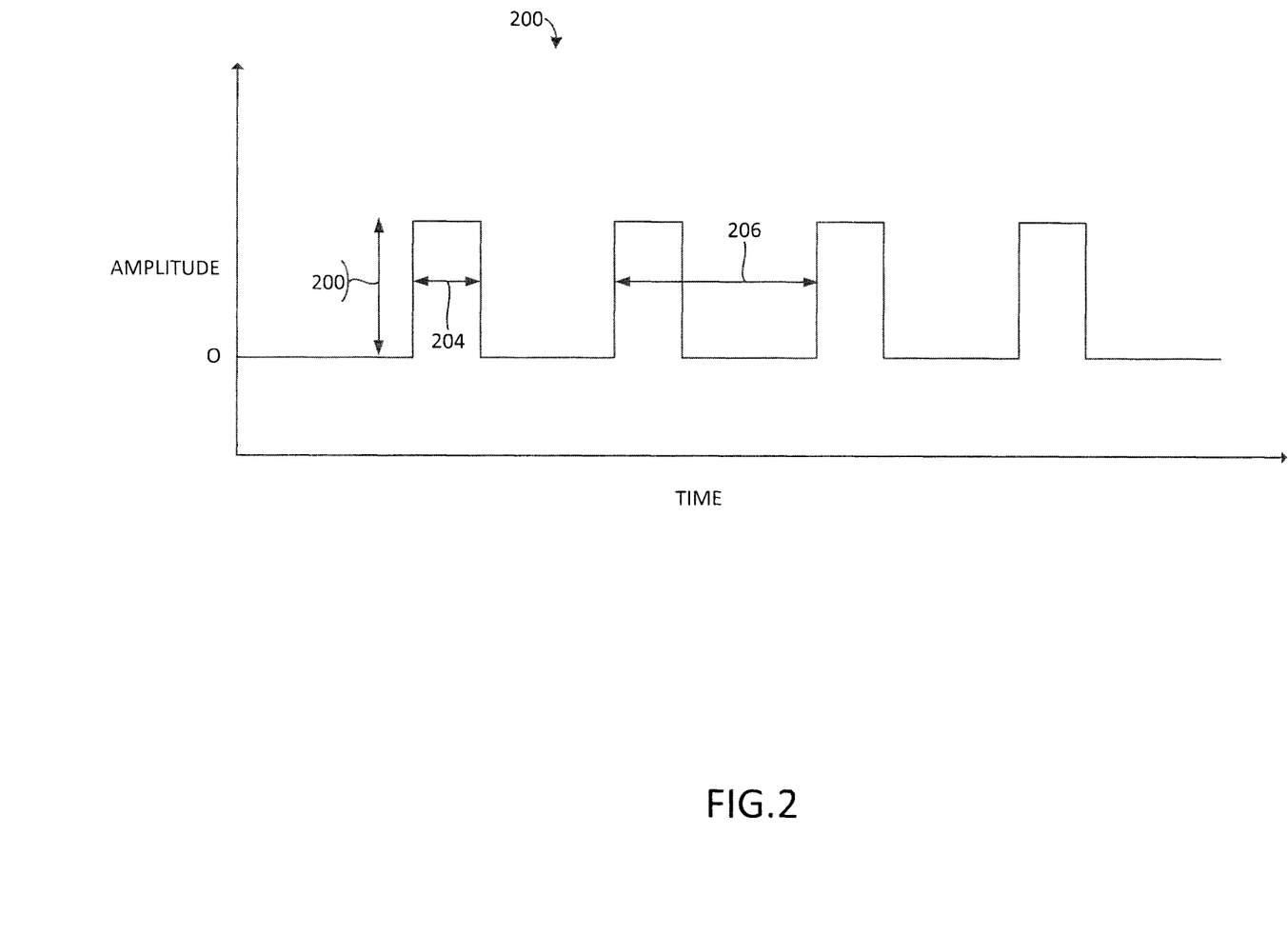
FIG. 2 illustrates an exemplary continuous pulse train signal, according to various embodiments of the invention.

With brief reference to FIG. 2, an exemplary continuous pulse train signal 200, or pulse signal 200, is shown. The pulse signal 200 may be a square wave, as shown, or may have a wave of any other shape. The pulse signal 200 may be periodic, as shown, or may be intermittent (i.e., multiple series of pulses separated by periods of no voltage).

The pulse signal 200 may have an amplitude 202. The amplitude 202 may be measured in volts, milliamps, or the like. Each of the pulses of the pulse signal 200 may have a pulse width 204. Likewise, if the pulse signal 200 is periodic, the pulse signal 200 may have a period 206 that corresponds to a frequency of the pulse signal 200.

Returning reference to FIG. 1, the wireless input-output port 120 may be capable of communicating with the remote device 110 via any wireless protocol such as a wireless communications protocol using short wavelength UHF radio waves and defined at least in part by IEEE 802.15.1 (e.g., the BLUETOOTH protocol maintained by Bluetooth Special Interest Group), a cellular signal, an infrared signal, an optical signal, or any other signal capable of transmitting and receiving information wirelessly.

The remote device 110 may be capable of updating operation of the stimulator 102. For example, the remote device 110 may be capable of providing instructions usable by the processor 112 to generate a new pulse signal.

In some embodiments, the wireless input-output port 120 may also be capable of receiving a wireless charging signal. In that regard, the remote device 110 may transmit a wireless charging signal which may be received by the wireless input-output port 120. The wireless input-output port 120 may then transmit the received wireless charging signal as electrical power to the power storage 116 for storage and later use, or may transmit the received wireless charging signal to the power transmitter 118 for transmission to the electrodes 104.

A novel feature of the current invention is to modulate a continuous stimulus train to match the dynamics of intracellular calcium ion oscillations of smooth muscle. As described herein, the location of the stimulating electrodes differs from conventional approaches by targeting an area proximal to the LES where the pacemaker region is located. By synchronizing stimulation to calcium oscillations, the oscillation frequency can be increased and smooth muscle contraction force may be significantly enhanced. The simplest modulation that may be used is intermittent on-and-off cycling.

Figure 3:
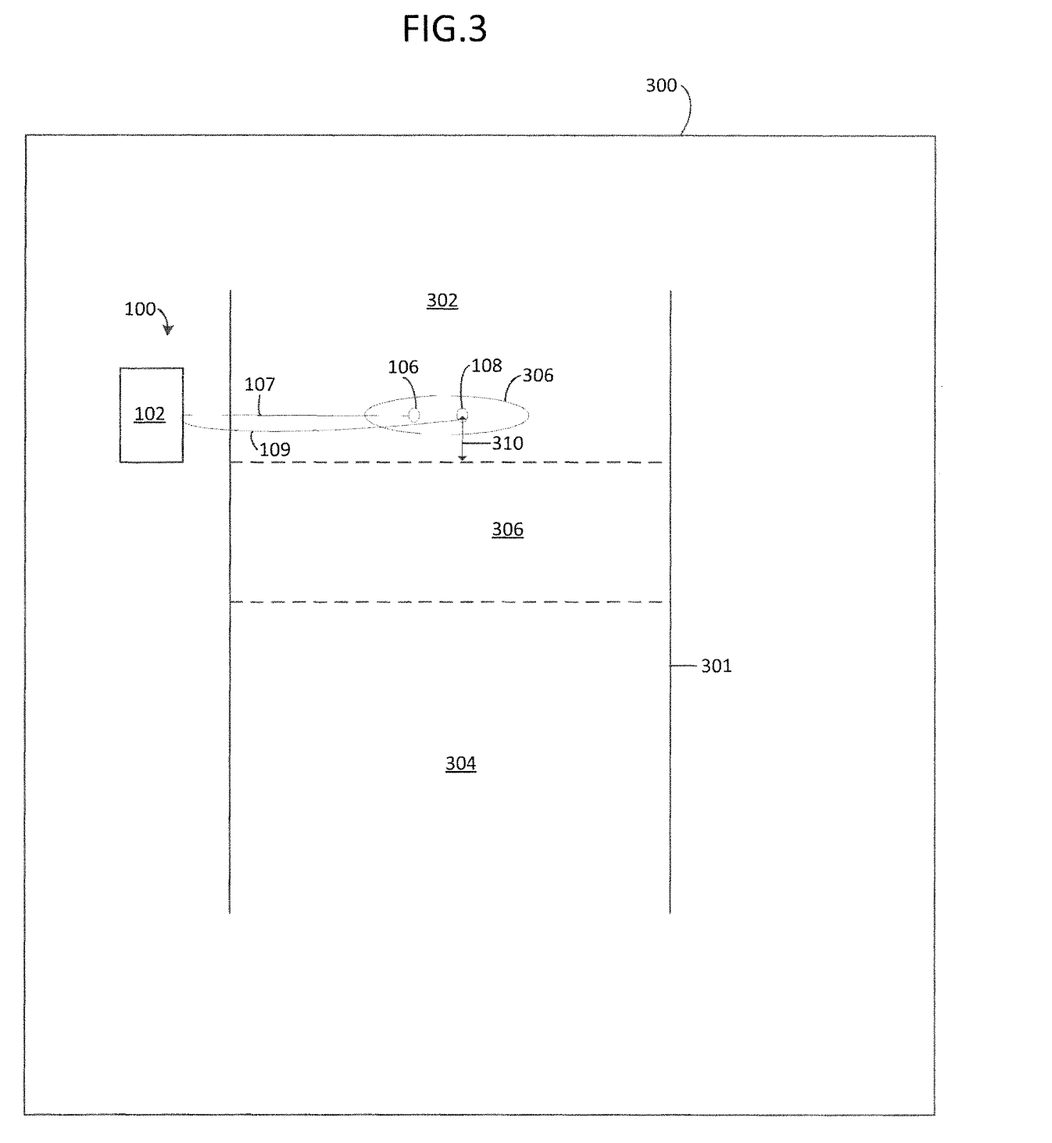
FIG. 3 illustrates an exemplary implementation of the system of FIG. 1, according to various embodiments of the invention.

Turning now to FIG. 3, exemplary implementation of the system 100 is shown. As mentioned above, the system 100 is designed to be utilized with a mammal to enhance sphincter closure via entrainment. FIG. 3 illustrates a portion of a gastrointestinal tract 301 of a body 300 of the mammal.

In particular, FIG. 3 illustrates an esophagus 302, a stomach 304, and a sphincter 306 located between the esophagus 302 and the stomach 304.

The system 100 may be designed to increase a pressure of the sphincter 306 to reduce the likelihood of acids from the stomach 304 escaping into the esophagus 302, a condition referred to as acid reflux disease.

The stimulator 102 may be implanted into the body 300 at a location near the gastrointestinal tract 301. The electrodes 106, 108 of the system 100 may be located in the esophagus 302 at a location above the sphincter 306. For example, the electrodes 106, 108 may be located a distance 310 from the sphincter 306. In some embodiments, the distance 310 may be between 0.5 centimeters (cm) and 5 cm (0.20 and 2 inches), between 1 cm and 3 cm (0.4 inches and 1.2 inches), between 1 cm and 2 cm (0.4 inches and 0.79 inches), or the like. As is known by one skilled in the art, the distance 310 may vary based on the size and dimensions of the specific mammal.

Pacemaker cells 308 (also referred to herein as a pacemaker region) may be located near the sphincter 306 and may control the opening and closing of the sphincter 306. In that regard, it may be desirable for the electrodes 106, 108 to be located near or on the pacemaker cells 308. For example, the electrodes 106, 108 may be conductive and may conduct the pulse signal generated by the stimulator 102 to the pacemaker cells 308.

Conventional systems for enhancing sphincter closure apply a continuous signal (i.e., a constant voltage or current signal) to the sphincter 306 itself. However, as discussed below, experiments have shown that applying a pulse signal (as opposed to a continuous signal) at a location above the sphincter 306 (as opposed to at or on the sphincter 306) provides significantly better results than use of the conventional systems.

Figure 4:
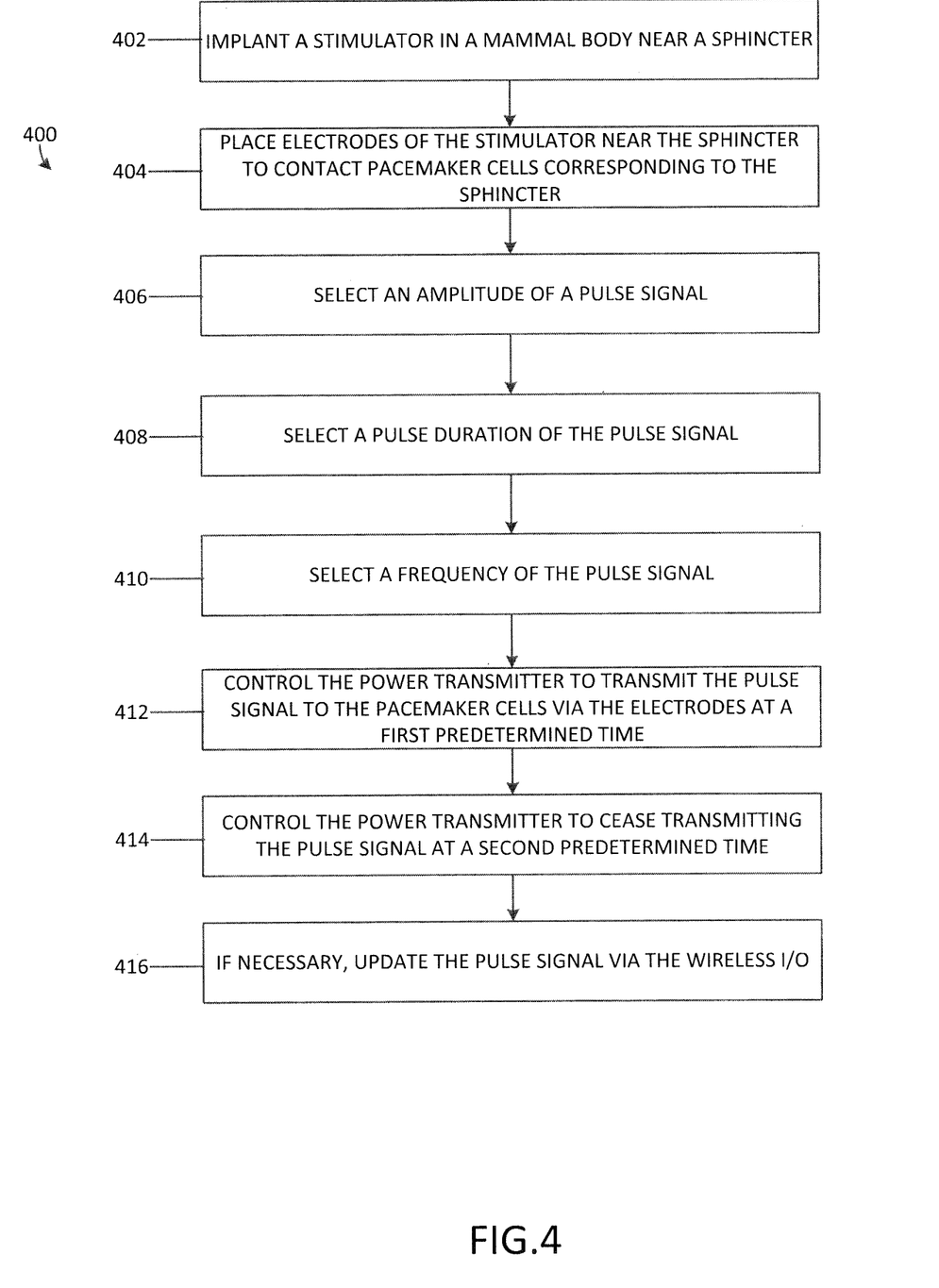
FIG. 4 illustrates a method for electrically enhancing sphincter closure by entrainment of pacemaker cells, according to various embodiments of the invention.

Turning now to FIG. 4, a method 400 for electrically enhancing sphincter closure by entrainment of pacemaker cells is shown. In block 402, a stimulator may be installed in a mammal body near a sphincter. For example, the sphincter may be an esophageal sphincter between an esophagus and the stomach, may be an anal sphincter between an anal canal and an anus, or the like. In some embodiments, the location for electrode placement is proximal (about 1-1.5 cm) to the LES site. In some embodiments, the electrode placement determination is made empirically by trial and error of applying stimulation to a location and observing whether the stimulation results in increased pressure of the sphincter.

In block 404, electrodes coupled to the stimulator via leads may be placed near the sphincter. For example, the electrodes may be placed above the sphincter in such a manner as to contact pacemaker cells that correspond to the sphincter. In some embodiments, placement of the electrodes may be performed by trial and error. For example, the electrodes may be placed in a first location, a pulse signal may be applied to the electrodes, and pressure applied by the sphincter may be measured by a catheter. If the measured pressure is insufficient, the electrodes may be placed in a new position, the pulse signal may be reapplied, and a new pressure may be measured. This process may continue until the measured pressure indicates that the electrodes are likely position sufficiently close to the pacemaker cells that correspond to the sphincter.

As described herein, previous approaches have specifically targeted the LES location, instead of the pacemaker or oscillatory region, as disclosed herein.

In block 406, an amplitude of the pulse signal may be selected. The amplitude may be selected based on a pain tolerance of the mammal in which the stimulator is implanted. For example, the electrodes may be placed in a desired location and a continuous signal (such as a signal of 5 milliamps) may be applied. The amplitude of the signal may be increased until the pain is intolerable (or the discomfort is undesirable) by the mammal (i.e., the signal reaches a threshold amplitude). Because the final pulse signal will be provided as pulses rather than a continuous signal, an amplitude above the threshold amplitude may be selected and may provide less discomfort than the continuous signal at the threshold amplitude. In some embodiments, the amplitude may be selected using a model of the stimulator and of the mammal to identify an ideal amplitude that provides desirable results.

In block 408, a pulse duration of the pulse signal may be selected. The pulse duration may be selected based on multiple variables such as a capacity of a power storage of the stimulator, effectiveness of various pulse durations, or the like. In some embodiments, the pulse duration may be selected using a model of the stimulator and of the mammal to identify an ideal pulse duration that provides desirable results.

In block 410, a frequency of the pulse signal (or a pulse pattern, if the pulse signal is nonperiodic) may be selected. The frequency may be selected based on multiple variables such as capacity of the power storage, the effectiveness of the various frequencies (or pulse patterns), or the like. In some embodiments, the frequency (or pulse pattern) may be selected using a model of the simulator and of the mammal to identify an ideal frequency (or pulse pattern) that provides desirable results.

In some embodiments, the pulse signal may only be transmitted at certain times of the day. For example, it may be desirable to increase closure of the sphincter at nighttime when the mammal may be resting in order to reduce the likelihood of acid flowing from the stomach to the esophagus. In that regard and in block 412, the power transmitter may be controlled by the processor to transmit the pulse signal to the pacemaker cells via the electrodes at a 1st predetermined time. For example, the predetermined times may be stored in the memory.

In block 414, the processor may control the power transmitter to cease transmitting the pulse signal at a $2^{nd}$ predetermined time. For example, the processor may be programmed to control the power transmitter to cease transmitting the pulse signal at a time that corresponds to a waking time of the mammal.

In some embodiments, the benefits of the method 400 (i.e., the enhanced sphincter closure) may continue for a period of time after application of the pulse signal to the pacemaker cells. For example, it may be determined that the enhanced sphincter closure continues for a period of 3 hours after the pulse signal has been applied for 20 minutes. In that regard, the processor may control the power transmitter to cease transmitting the pulse signal 20 minutes after the pulse signal has begun transmission, and to again begin transmitting the pulse signal 3 hours after cessation.

Occasionally, updating of the stimulator may be desirable. For example, a new pulse signal may be determined that provides advantages over a current pulse signal. In that regard and in block 416, the pulse signal may be updated via the wireless input output port such that the new pulse signal is provided to the processor of the stimulator. Additionally and in some embodiments, power may be transmitted to the stimulator in block 416. For example, power may be transmitted to the wireless input-output port via a wireless charging technique. As another example, the stimulator may be removed and a battery of the stimulator may be replaced.

In some embodiments, an empirical approach may be taken to determining the parameters of the stimulus to the pacemaker regions or cells (e.g., the frequency, amplitude, and duration of the stimulus). In these embodiments, various combinations of parameters may be tried for efficacy, and the most effective combination of parameters may be used to entrain the pacemaker cells.

In other embodiments, a modeling approach may be taken to determining the parameters. The modeling approach described herein may be performed using a computer designed for determining the parameters used to entrain pacemaker cells. The computer may include a processor and a non-transitory memory configured to store instructions to be executed by the processor.

Figure 5:
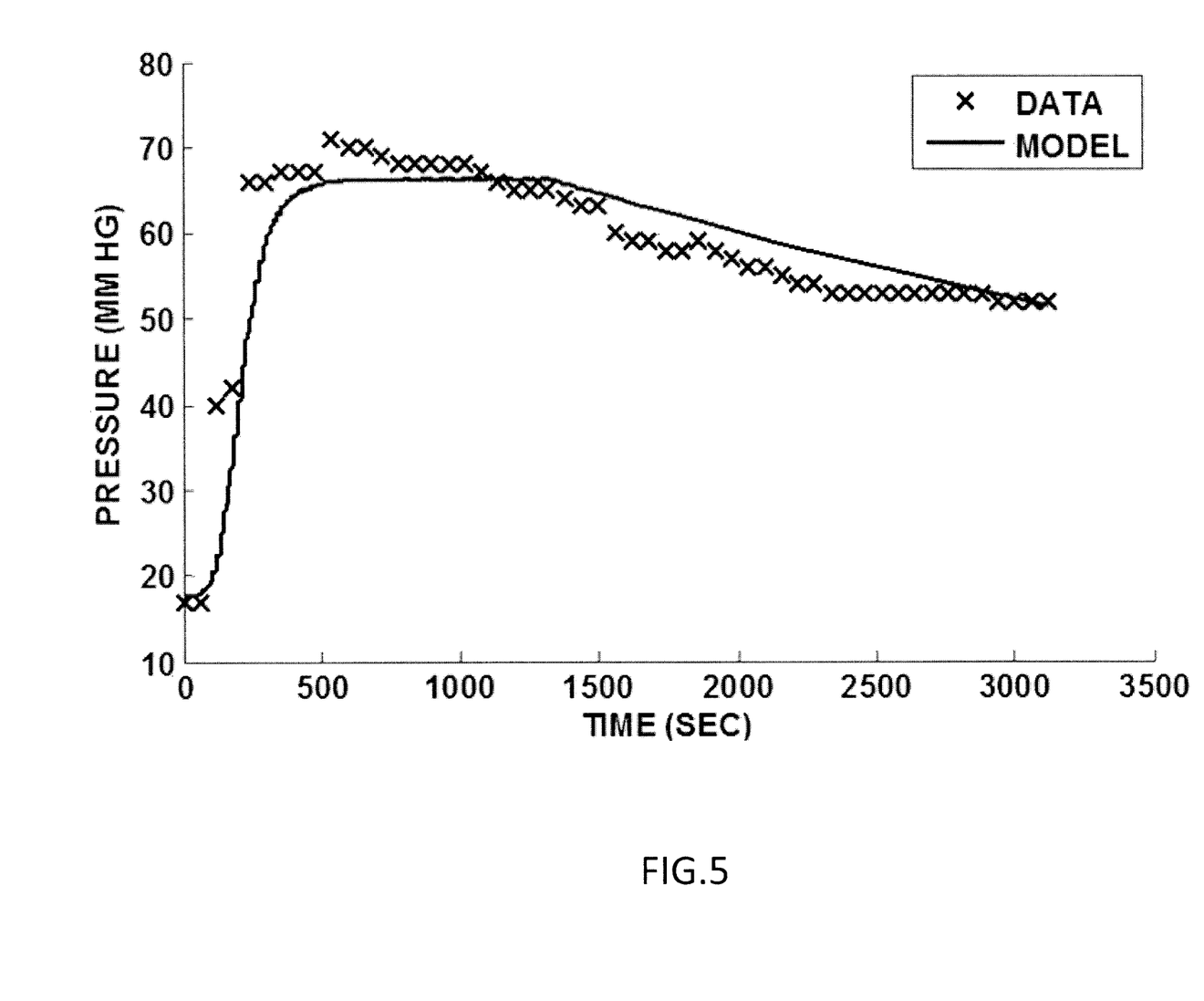
FIG. 5 illustrates model predictions and collected data for determining optimal stimulation parameters, according to various embodiments of the invention.

A mathematical model may be used to predict the experimental results of applying a stimulus to the pacemaker region according to various parameters. The conformity between model predictions and collected data is shown in FIG. 5.

A significant portion of the mathematical model involves describing calcium dynamics and oscillatory behavior. An important component leading to unstable (oscillatory) behavior is calcium-induced-calcium release. This characteristic corresponds to "positive feedback" and instability. The mathematical model parameters were chosen to match the approximately 10-minute transient response time. The duration of an individual calcium pulse as shown in FIG. 5 was found to limit the maximum possible entrainment frequency.

The mathematical model provides a method to predict the optimized stimulation parameters for entrainment. This is not a trivial task as the model is highly non-linear. Small changes in stimulation parameters, such as amplitude of stimulation pulses or burst repetition rate, can lead to entrainment success or failure. In a successful animal trial, for example, an exhaustive trial and error adjustment of different parameters was used to achieve entrainment. Experimental measurement of phase response curves to predict a non-linear oscillator response to specific electrical stimulation have been previously used. However, the systems and method described herein use a non-linear model instead which can be used to predict responses to all inputs of interest. The listed model parameter values are included to illustrate the methodology, but the specific parameters used depend on the specific targeted type of smooth muscle.

A first, simplified model may be used based on a gastric smooth muscle developed by Corrias and Buist (Corrias, A. and M. Buist, *A quantitative model of gastric smooth muscle cellular activation*, Ann. of BME 35: 1595-1607, 2007) as simplified by Du et al. (Du, P., G. O'Grady, L. Cheng, A. Pullan, and J. Chen, *Effects of electrical stimulation on isolated rodent gastric smooth muscle cells evaluated via a joint computational simulation and experimental approach*, Am. J. Physiol. Gastrointest Liver Physiol 297: G672-G680, 2009), the contents of which are incorporated by reference in their entirety. The main simplification is the assumption of a negligible contribution of sodium membrane channels. The following two differential equations are used:

$$C_m dV_m/dt = -(I_{ion} + I_{stim}) \quad (A.1)$$

$$I_{ion} = I_{CaL} + I_{LVA} + I_{Kr} + I_{Ka} + I_{Kb} + I_{NSCC}$$

$$dCa_i/dt = -(I_{CaL} + I_{CaT})/(2FV_c) - I_{CaExt} \quad (A.2)$$

where $Ca_i$=intracellular calcium concentration, and $V_m$=membrane potential.

$I_{stim}$=external current stimulation.

The majority of the variable and parameter definitions may be kept the same as Corias and Buist so a complete list is not repeated herein. Most of the assumed parameter values may be kept the same as what was used by Du et al., except for the description of the non-selective cationic channels (NSCC), Interstitial Cells of Cajal (ICC) and membrane calcium channels. A change in NSCC and ICC is made to obtain a resting membrane potential of −50 my corresponding to the LES, rather than −70 my for the rat gastric smooth muscle. The following modification is used to describe $I_{NSCC}$:

$$I_{NSCC}=1.1(Vm+V_{ICC}) \quad (A.3)$$

$V_{ICC}$ is set equal to a constant 50 my or varied with time to simulate interstitial cell mediated slow potential changes. The L type membrane calcium channel model is described by:

$$I_{CaL}=g_{CaL}d^2f_{Ca}(0.8f_1+0.2f_2)(V_m-E_{CaL}) \quad (A.4)$$

$$f_{Ca}=1/(1+[Ca]_i/K_{d,CaL})^4 \quad (A.5)$$

$$d_\infty=1/(1+\exp(-(V_m+22)/7)) \quad (A.6)$$

$$f_\infty=1/(1+\exp(-(V_m+38)/7)) \quad (A.7)$$

$$\tau_d=2.29+5.7/(1+(V_m+29.97)/9)^2) \quad (A.8)$$

$$\tau_{f1}=12 \text{ msec} \quad (A.9)$$

$$\tau_{f2}=90.97(1-1/((1+\exp((V_m+13.97)/45.38)))(1+\exp(-(V_m+9.5)/3.39))) \quad (A.10)$$

$$dd/dt=(d_\infty-d)/\tau_d \quad (A.11)$$

$$df_1/dt=(f_\infty-f_1)/\tau_{f1} \quad (A.12)$$

$$df_2/dt=(f_\infty-f_1)/\tau_{f1} \quad (A.13)$$

Again, use of modeling may be performed by a computing device configured specifically for determining optimal parameters for pulsed stimulation of pacemaker cells. Equations A.1 and A.2 may be used in these models. The corresponding real-world situations the models are based on have a complexity and time-urgency such that the modeling may not be performed by a human being using paper and pen.

A second, intracellular calcium release model may also be used to predict optimal stimulation parameters for the systems and methods described herein.

The Li and Rinzel (Li, Y. and J. Rinzel, *Equations for $InsP_3$ receptor-mediated $[Ca^{2+}]_i$ oscillations derived from a detailed kinetic model: a Hodgkin-Huxley like formalism*, J. Theor. Biol. 166: 461-473, 1994) (incorporated by reference in its entirety) minimal model of $Insp_3$ receptor mediated intracellular calcium oscillations may be added to the first, simplified model. This may be accomplished by adding an intracellular calcium release current $I_{ICR}$ to equation A.1 and A.2 and a time scale parameter $K_{tscale}$:

$$C_m dV_m/dt=-(I_{ion}-I_{stim}-2FV_cK_{tscale}I_{ICR}) \quad (B.1)$$

$$dCa_i/dt=-(I_{CaL}+I_{CaT})/(2FV_c)-I_{CaExt}+K_{tscale}I_{ICR} \quad (B.2)$$

The resultant model then accounts for both membrane potential and $InsP_3$ mediated calcium dynamics. $I_{ICR}$ corresponds to $dCa_i/dt$ of the original Li and Rinzel model which assumed a constant membrane potential:

$$I_{ICR}=[v_1([IP_3]/([IP_3]+d_{ip3}))^3(Ca_i/(Ca_i+dact))^3h^3+v_2] \\ [c_0-(1+c_1)Ca_i]-v_3Ca_i^2/(k_{er}^2+Ca_i^2)+\varepsilon[j_{in}-v_4Ca_i^2/(k_{pl}^2+Ca_i^2)] \quad (B.3)$$

$$h=d_{inh}/(Ca_i+d_{inh}) \quad (B.4)$$

$$dc_0/dt=K_{tscale}\varepsilon[j_{in}-v_4Ca_i^2/(k_{pl}^2+Ca_i^2)] \quad (B.5)$$

where h=fraction of channels not yet activated by $Ca_i$ which was assumed to rapidly reach steady state conditions and $c_0$=total free calcium per cytosolic volume, primarily the endoplasmic reticulum intracellular storage. Table B.1 lists the assumed parameter values.

TABLE B.1

Parameter values for model including intracellular calcium release.

| Parameter | Value | Parameter | Value | Parameter | Value |
|---|---|---|---|---|---|
| $v_1$ | 50 sec$^{-1}$ | $d_{ip3}$ | 0.2 μM | $k_{pl}$ | 0.1 μM |
| $v_2$ | .02 sec$^{-1}$ | $d_{act}$ | .48 μM | $K_{tscale}$ | 4.50E-05 |
| $v_3$ | .7 sec$^{-1}$ | $d_{inh}$ | .48 μM | $IP_3$ | .55 μM |
| $v_4$ | 1.6 sec$^{-1}$ | $k_{er}$ | .15 μM | $\varepsilon$ | 0.01 |
| $j_{in}$ | 1.1 μM/sec | a | 4 sec$^{-1}$ | | |

A third, force output model may also be used to predict optimal stimulation parameters for the systems and methods described herein.

The Hai- and Murphy (Hai, C. and R. Murphy, *Cross-bridge phosphorylation and regulation of latch state in smooth muscle*, Am. J. Physiol. Cell Physiol. 254: C99-C106, 1988) model is used with phosphorylation rate constants made a function of intracellular calcium concentration, as justified by Bursztyn et al. (Bursztyn, L., O. Eytan, A. Jaffa, and D. Elad, *Mathematical model of excitation-contraction in a uterine smooth muscle cell*, Am. J. Physiol. Cell Physiol. 292: C1816-C1829, 2007) for uterine smooth muscle. Each reference is incorporated by reference in its entirety. The differential equations used were:

$$d[M]/dt=-K_1[M]+K_2[M_p]+K_7[AM] \quad (C.1)$$

$$d[M_p]/dt=K_4[Am_p]+K_1[M]-(K_2+K_3)[M_p] \quad (C.2)$$

$$d[Am_p]/dt=K_3[M_p]+K_6[AM]-(K_4+K_5)[Am_p] \quad (C.3)$$

$$d[AM]/dt=K_5[Am_p]-(K_7+K_6)[AM] \quad (C.4)$$

where the variables describe myosin, M=free unphosphorylated and $M_p$ phosphorylated cross bridges, AM=dephosphorylated and $Am_p$ phosphorylated latch bridges. Normalized muscle force F is calculated by:

$$F=AM+Am_p \quad (C.4)$$

$$1.0=M+M_p+AM+Am_p \quad (C.5)$$

Based on experimental data, the following were assumed:

$$K_1=K_6, K_2=K_5, \text{ and } K_3/K_4=4.$$

These constraints lead to a maximum normalized force $F_{max}$=0.8.

The relationship used to relate phosphorylation rate constants $K_1$ and $K_6$ to intracellular calcium concentration $Ca_i$ was:

$$K_1=K_6=[Ca_i]^{nM}/([Ca_i]^{nM}+[Ca_{1/2MLCK}]^{nM}) \quad (C.6)$$

where nM=8.7613 and $Ca_{1/2MLCK}$=256.98 nM.

Any of the mathematical models described herein may be used in determining the parameters for electrical stimulation of the pacemaker cells.

Figure 6:
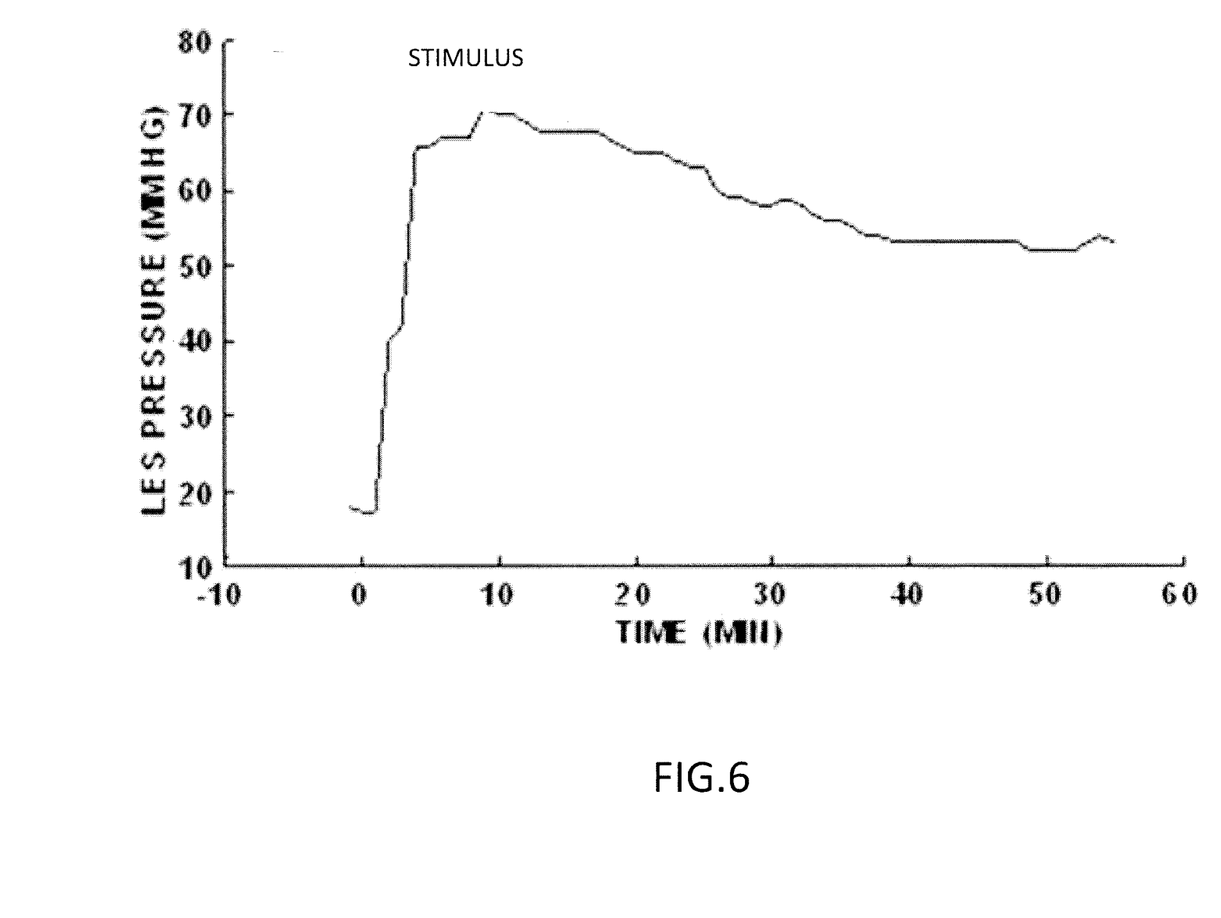
FIG. 6 illustrates measured response of closing pressure in the esophagus in response to a first set of stimulation parameters, according to various embodiments of the invention.

An experiment was conducted using the systems and methods described herein. A pacemaker device developed for stimulation of the lower esophageal sphincter to treat GERD (gastroesophageal reflux disease) was implanted in a dog. Following recovery from surgery, electrical stimulation was tried where the conventional stimulation (215 microsecond pulses, 20 Hz repetition frequency, 7 mA) was intermittently applied (8 seconds on and 8 seconds off) for 20 minutes followed by stimulation turned off and recovery monitored. The measured response of closing pressure in the esophagus is shown in FIG. 6.

What is notable is the high level of closing pressure of 70 mm Hg achieved (20 mm Hg is the normal level). No other electrical stimulation method has resulted in a higher closing pressure. This level of stimulation is at the same power level used for conventional delivery, which leads to insignificant pressure changes in humans (17.8 mm Hg to 22.6 mm Hg). The intermittent on and off times were specifically chosen to match human intracellular calcium on and off measurements. The oscillations in calcium concentration and forces were spontaneously generated. These human force responses also resemble dog responses and justifies using dog responses to guide human therapy. A maximum depolarization of the pacemaker has led to an increase of pacemaker oscillation to 4 times per minute (15 second period). This is then the maximum expected oscillation frequency which motivated the experimental use of a 16 second period. Spontaneous oscillation frequency was 3 times per minute, which sets a lower limit of about 20 seconds. A lower frequency may be possible, but is not expected to maximize contraction.

In the same animal, when the stimulus level was reduced to 5 mA with the other parameters kept the same, the pattern of the response changed to what is shown in FIG. 7. In this case, contraction occurred after the stimulation was discontinued. This type of response pattern has been observed previously and is called an "off" contraction. However, no previous research has reported such a large "off" contraction and the specific stimulation used herein prior to the "off" contraction was never previously tried. Electrical stimulation may lead to both excitatory and inhibitory responses, with excitatory responses being more prolonged and dominating at the end of stimulation. Further enhancement based on the "off" contraction may be possible. An "off" contraction was not observed for 10 minutes following the end of stimulation, so enhancement may be possible by cycling on and off periods with this 10-minute period in mind. There has not been any previous teachings of a method to enhance or use the "off" contraction as taught herein.

The collected data shows that stimulation based on entrainment leads to significant enhancement of sphincter closing pressure. In this experiment, the 8 second on and 8 second off intermittent train is close to the maximum possible frequency. Also in this experiment, the 7 mA stimulus amplitude was large enough to entrain and increase the frequency to the maximum possible frequency. The full entrainment and frequency increase required approximately 10 minutes to occur. That this was the maximum frequency was verified by trying different on-off durations leading to a lower closing pressure.

As described herein, a simple intermittent on-and-off cycling modulation may be used by the system. This was found to work in experiments when the stimulation pulse amplitude was large enough and the frequency was set to the maximum possible for entrainment. For example, for a chronic dog, a stimulus train of 215 microsecond pulses, frequency of 20 Hz, and 7 mA modulated 8 seconds on and 8 seconds off (3.75 cycles/min) led to the highest measured closing pressure at the LES, suggesting complete one-to-one entrainment. In dogs, a maximum frequency of 5.8 cycles/min may be possible when stimulated by more than depolarization. Using depolarization alone, 4 cycles per minute may be the limit for entrainment.

The current level, pulse duration, and frequency of continuous stimulation may be adjusted at the maximum levels which can be tolerated by the patient. Since power is decreased 50% by modulation, the current level may be increased (e.g., from 5 mA to 7 mA) to maintain the same power level. In experiments involving a dog, this did not lead to any visible increased discomfort in the awake animal. Use of a modulated or burst mode then allows a higher current to be used when power is kept the same. As indicated above, at low levels of stimulation, additional on-and-off cycling with periods each 5-15 minutes long may be used to enhance the expected dominance of "off" contraction. The mathematical model described herein and used to guide parameter settings may be an optimal guide to achieve entrainment. This is due to the non-linear interactions of the parameters which lead to non-obvious results. This was emphasized by the experimental results in FIG. 7 where a relatively small change in stimulation amplitude (5 mA to 7 mA) led to a completely different response, as compared to the results of FIG. 6.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for electrically stimulating a smooth muscle, comprising:
   generating, by a power transmitter, a continuous pulse train signal having pulses and pulse intervals between the pulses, the pulses and the pulse intervals being generated at a pulse frequency;
   modulating, by a processor, the continuous pulse train signal at a modulation frequency to match dynamics of intracellular calcium ion oscillations in the smooth muscle; and
   transmitting, by the power transmitter, the modulated continuous pulse train signal to at least one electrode contacting a collection of pacemaker cells corresponding to the smooth muscle to entrain the collection of pacemaker cells to increase an oscillation frequency of the intracellular calcium ion oscillations.

2. The method of claim 1 wherein modulating the continuous pulse train signal at the modulation frequency includes transmitting the continuous pulse train signal for a first time period and ceasing transmission of the continuous pulse train signal for a second time period, a sum of the first time period and the second time period equaling a modulation period corresponding to the modulation frequency.

3. The method of claim 2 wherein the first time period is equal to a duration of a rising phase to a peak of the intracellular calcium ion oscillations to within about 0.5 to 15 seconds.

4. The method of claim 2 wherein the first time period is equal to the second time period.

5. The method of claim 1 wherein the modulation frequency is between 1 cycle per minute and 60 cycles per minute.

6. The method of claim 1 wherein modulating the continuous pulse train signal at the modulation frequency includes modulating the continuous pulse train signal at a minimum modulation frequency that is less than a maximum modulation frequency and continuously or periodically increasing the modulation frequency to the maximum modulation frequency over a period of time.

7. The method of claim 6 wherein the period of time is between 1 minute and 60 minutes.

8. The method of claim 6 wherein a period of time of stimulation is repeated one or more times following a period of no stimulation.

9. The method of claim 1 wherein each of the pulses has a duration between 10 to 1,000 microseconds and the pulse frequency is between 1 hertz and 50 hertz.

10. The method of claim 1 further comprising using a mathematical model to determine optimal stimulation parameters.

11. The method of claim 1 further comprising:
positioning the at least one electrode to a location near a sphincter to be stimulated; and
generating, by a stimulator, the modulated continuous pulse train signal,
wherein transmitting the modulated continuous pulse train signal to the at least one electrode enhances closure of the sphincter.

12. The method of claim 11 wherein the sphincter is an esophageal sphincter located between a stomach and an esophagus of a mammal, and the location is located above the esophageal sphincter in the esophagus.

13. The method of claim 1 further comprising transmitting the continuous pulse train signal to the at least one electrode at a first predetermined time, and ceasing to output the continuous pulse train signal at a second predetermined time.

14. The method of claim 11 wherein the sphincter is an anal sphincter located between an anal cavity and an anus.

15. A system for electrically stimulating a sphincter, comprising:
a stimulator having a housing configured to be implanted in or worn on a mammal and having a power transmitter configured to output a continuous pulse train signal having pulses and pulse intervals between the pulses; and
at least one electrode electrically coupled to the power transmitter and configured to contact a collection of pacemaker cells corresponding to the sphincter at a location near the sphincter and to transmit the continuous pulse train signal to the collection of pacemaker cells at the location near the sphincter to enhance closure of the sphincter.

16. The system of claim 15 wherein the sphincter is an esophageal sphincter located between a stomach and an esophagus of the mammal, and the location is located above the esophageal sphincter in the esophagus.

17. The system of claim 15 wherein the sphincter is an internal anal sphincter located between an anal cavity and an anus.

18. The system of claim 15 wherein the stimulator further includes a processor configured to control the power transmitter to output the continuous pulse train signal at a first predetermined time and to cease outputting the continuous pulse train signal at a second predetermined time.

19. The system of claim 15 wherein the sphincter is an internal urethral sphincter located near an output of a bladder.

\* \* \* \* \*